US009168391B2

(12) United States Patent
Henning et al.

(10) Patent No.: US 9,168,391 B2
(45) Date of Patent: Oct. 27, 2015

(54) MOBILE X-RAY UNIT

(75) Inventors: Johan Henning, Veenendaal (NL); Bas Woudstra, Vaassen (NL)

(73) Assignee: NUCLETRON B.V. (NL)

( * ) Notice: Subject to any disclaimer, the term of this patent is extended or adjusted under 35 U.S.C. 154(b) by 676 days.

(21) Appl. No.: 13/335,152

(22) Filed: Dec. 22, 2011

(65) Prior Publication Data

US 2012/0163556 A1 Jun. 28, 2012

Related U.S. Application Data

(60) Provisional application No. 61/426,910, filed on Dec. 23, 2010.

(30) Foreign Application Priority Data

Dec. 22, 2010 (NL) ..................................... 2005904

(51) Int. Cl.
| | |
|---|---|
| *H05G 1/02* | (2006.01) |
| *A61B 6/08* | (2006.01) |
| *A61N 5/10* | (2006.01) |
| *G21K 1/02* | (2006.01) |

(52) U.S. Cl.
CPC ............ *A61N 5/1049* (2013.01); *A61N 5/1083* (2013.01); *A61N 2005/1056* (2013.01); *A61N 2005/1091* (2013.01)

(58) Field of Classification Search
USPC ........... 378/65, 140, 143, 161, 196–198, 206, 378/210; 250/307.08, 370.09, 339.05, 250/339.06, 340, 341.1, 362, 363.01, 250/363.02, 393, 395, 493.1, 522, 526
See application file for complete search history.

(56) References Cited

U.S. PATENT DOCUMENTS

| | | | | |
|---|---|---|---|---|
| 7,764,765 | B2 * | 7/2010 | Ohta et al. ...................... | 378/91 |
| 8,194,823 | B2 * | 6/2012 | Ohta et al. ...................... | 378/91 |
| 8,520,801 | B2 * | 8/2013 | Henning ......................... | 378/65 |
| 2002/0150215 | A1 | 10/2002 | Barnes et al. | |
| 2003/0048875 | A1 | 3/2003 | Mihara et al. | |

(Continued)

FOREIGN PATENT DOCUMENTS

| | | |
|---|---|---|
| EP | 2005992 | 12/2008 |
| GB | 2284331 | 5/2005 |
| WO | WO 2007/062900 | 6/2007 |
| WO | WO 2008/118198 | 10/2008 |

OTHER PUBLICATIONS

Search Report and Written Opinion in related Netherlands Application No. 2005904 dated May 28, 2011 (10 pages).

(Continued)

*Primary Examiner* — Bernard E Souw
(74) *Attorney, Agent, or Firm* — Finnegan, Henderson, Farabow, Garrett & Dunner, LLP

(57) ABSTRACT

One embodiment of the present disclosure is directed to a mobile X-ray unit. The mobile X-ray unit may include a base having a control unit and a power supply. The mobile X-ray unit may further include an articulated arm associated with the base. The articulated arm may be coupled to an X-ray applicator having an X-ray tube. The X-ray tube may include a target for generating an X-ray beam, a collimator for shaping the X-ray beam, and an exit surface through which the X-ray beam is configured to exit the X-ray tube. The mobile X-ray unit may have at least one light source configured to illuminate at least a portion of the X-ray beam emitted from the exit surface.

32 Claims, 13 Drawing Sheets

(56) References Cited

U.S. PATENT DOCUMENTS

| | | | |
|---|---|---|---|
| 2007/0029492 A1* | 2/2007 | Abe | 250/370.09 |
| 2007/0076851 A1 | 4/2007 | Pellegrino | |
| 2012/0163538 A1* | 6/2012 | Henning | 378/65 |
| 2012/0163539 A1* | 6/2012 | van der Veen et al. | 378/65 |
| 2012/0163540 A1* | 6/2012 | van der Veen et al. | 378/65 |
| 2012/0163551 A1* | 6/2012 | Jager | 378/143 |
| 2012/0195405 A1* | 8/2012 | Woudstra et al. | 378/65 |

OTHER PUBLICATIONS

TOPEX, Inc., "SRT 100 Superficial Radiotherapy System for the Treatment of Skin Cancer," http://www.harpell.ca/wp-content/uploads/2009/11/topexbrochure_v10.pdf, (6 pages).

Topex, Inc., "Regulatory Information," http://www.tpoexmedical.com/product2.html, 2007 (1 page).

* cited by examiner

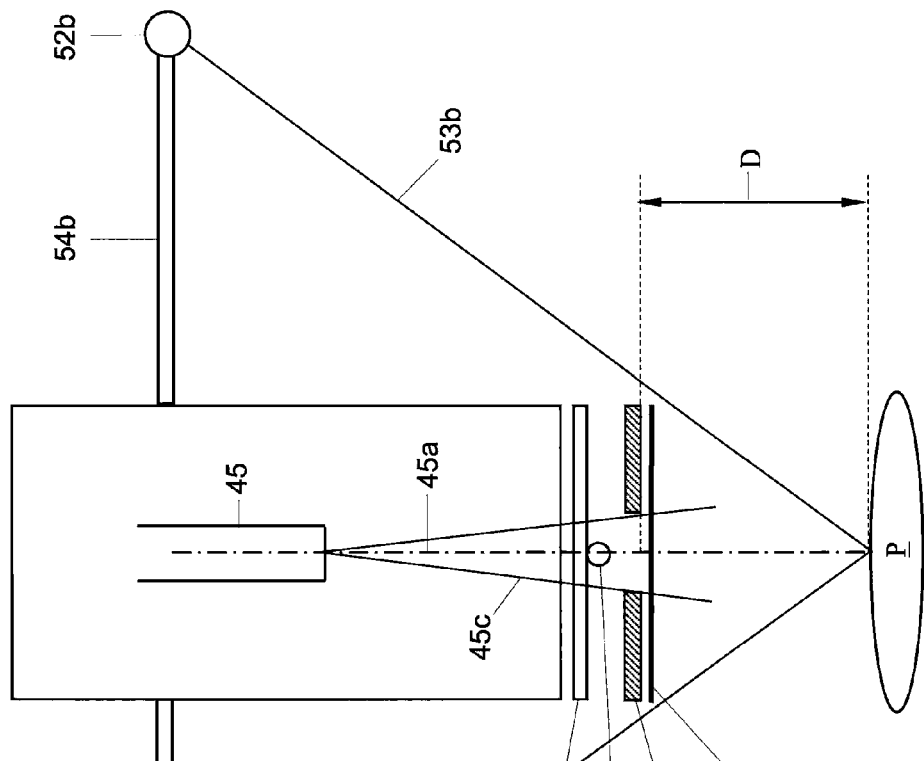
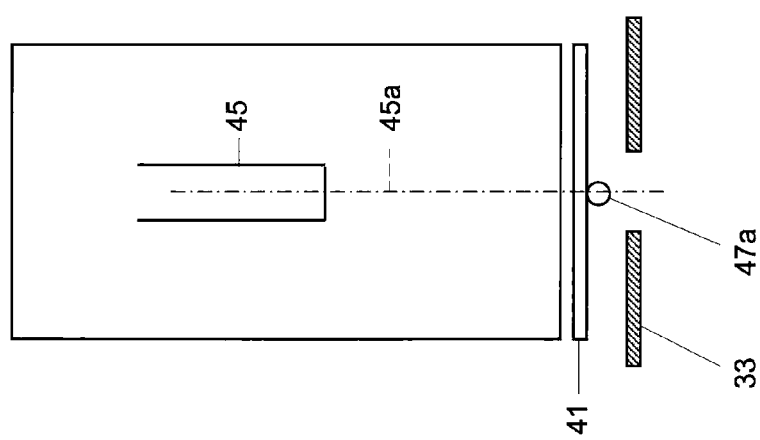
Fig. 3c
Fig. 3b

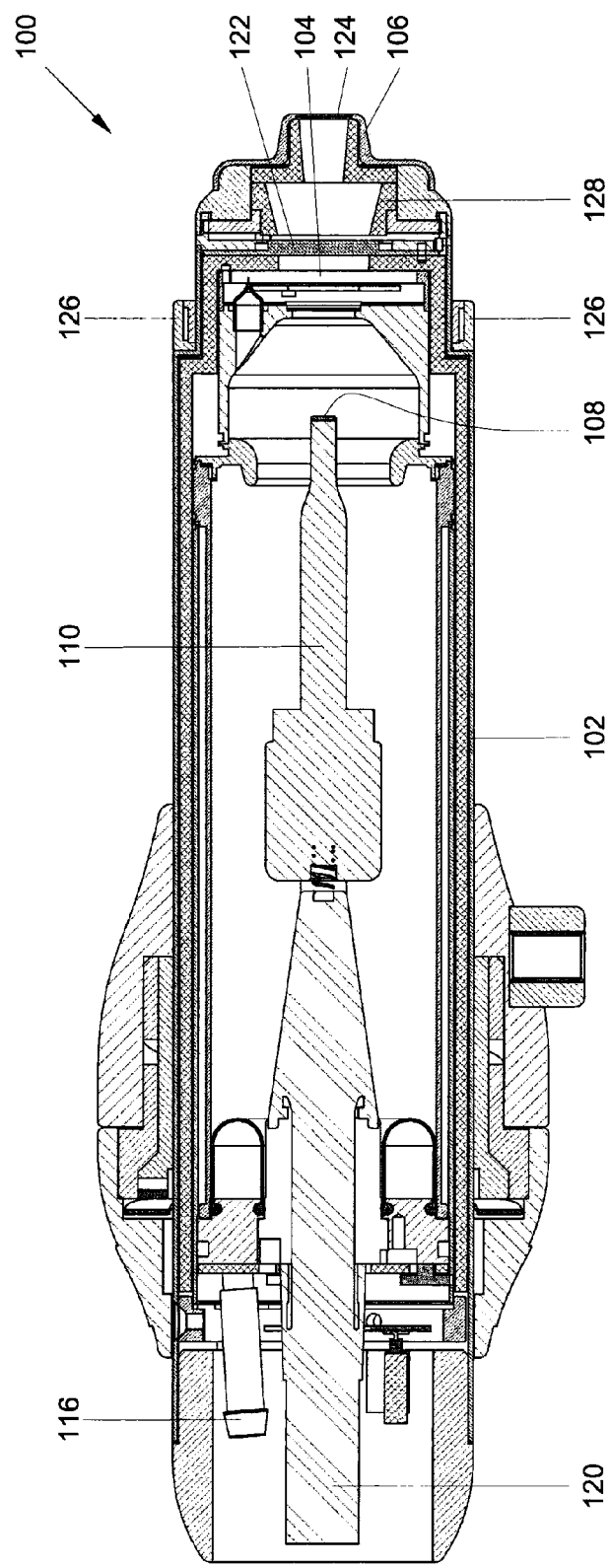
Fig. 8, E-E

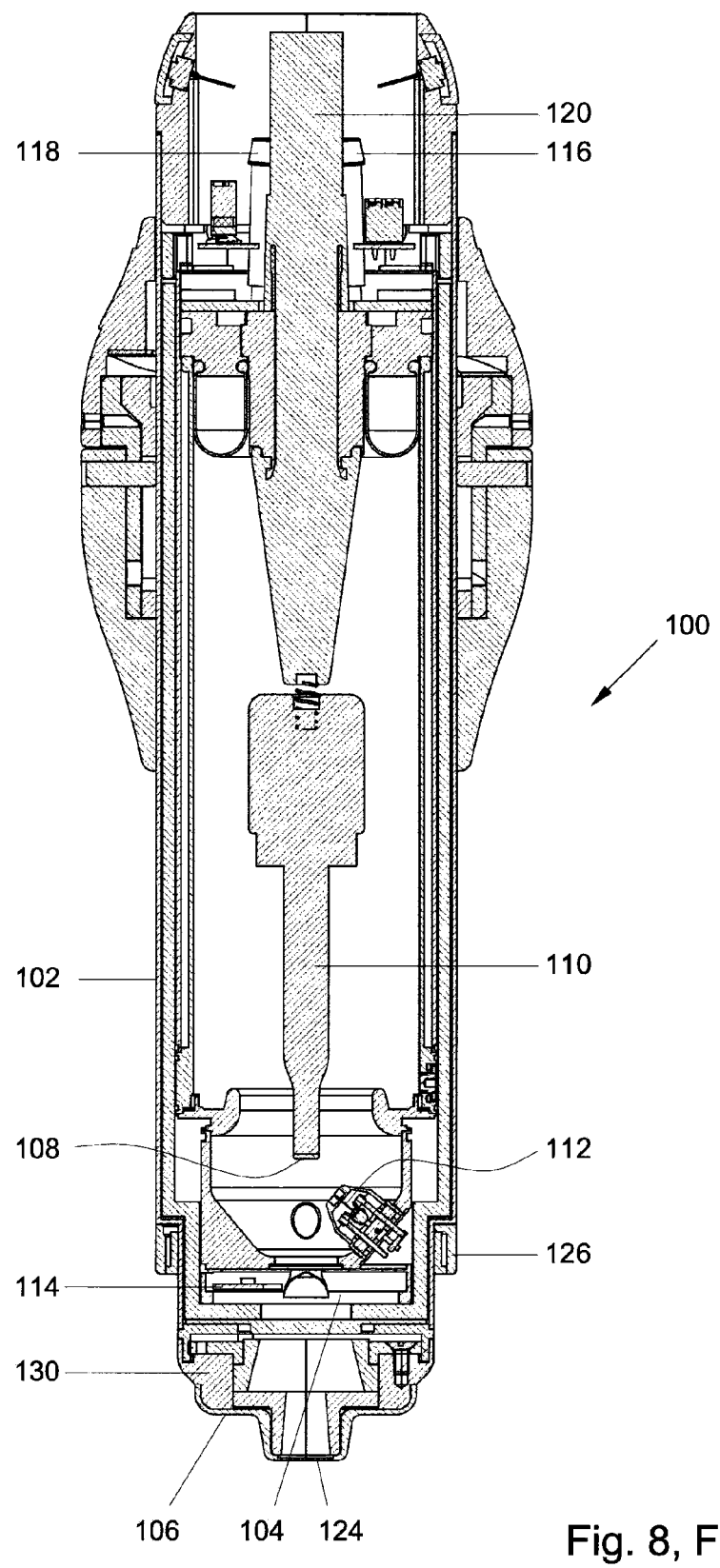
Fig. 8, F-F

MOBILE X-RAY UNIT

CROSS-REFERENCE TO RELATED APPLICATIONS

This application claims the benefit of priority based on U.S. Provisional Patent Application No. 61/426,910, filed Dec. 23, 2010, and Netherlands Patent Application No. 2005904, filed Dec. 22, 2010, which are all incorporated herein by reference.

FIELD OF THE INVENTION

The present disclosure relates generally to a mobile X-ray unit. The present disclosure further relates to a method of visualization of an X-ray beam.

BACKGROUND OF THE INVENTION

The incidence rate of skin cancer has substantially increased in the last decade of the $20^{th}$ century. It is appreciated that over 1.3 million new skin cancers are diagnosed annually, which is increasing at a rate of about 5% per year. Increased exposure to the sun without skin protection and a decreased ozone layer are regarded as the main causes of this increase—a problem estimated to be costing over 1 billion Euros in annual medical treatment expenses. Over 80% of skin cancers occur in the head and neck regions with 50% occurring in patients over 60 years of age. It is expected that a portion of the senior population will double in year 2025 compared to the present demographics. Because of the growing incidence of skin cancer and increasing share of the senior population in the overall demographics, much focus has been placed on cancer treatments and cancer treatment logistics.

Non-proliferative cancers, which are defined by substantially superficial lesions, may be treated in different ways. In one example, non-proliferative cancers may be treated surgically. Surgery, may, however, have certain drawbacks, such as, for example, long waiting lists, complications related to post-treatment care, and risk of infection. Alternatively, patients may undergo irradiation using electrons of soft X-rays. Irradiation may have an advantage of being non-invasive and of a short duration (a treatment session may be as short as 2 to 4 minutes). It will be appreciated that usually the integral treatments using radiotherapeutic techniques may require a number of sessions.

Recently, the use of a mobile and portable X-ray unit has been suggested, which may be used inside a hospital radiotherapy department. An embodiment of such portable unit is described in U.S. 2007/0076851. Existing X-ray units include an X-ray source and a filtering device having a plurality of filters rotatably arranged with respect to a focal point of the X-ray tube for changing filtering characteristics on demand. The plurality of filters are arranged in a filtering device, which is transversely arranged with respect to a longitudinal axis of the X-ray tube. These units, while effective, may have certain drawbacks. For example, it may be difficult to delineate the X-ray beam emitted from the X-ray applicator and a treated region on the patient.

SUMMARY OF THE INVENTION

It is an object of the present disclosure to provide a mobile X-ray unit configured to delineate between at least a portion of the actual X-ray beam emitted from the X-ray applicator and a target region on the patient. It is a further object of the present disclosure to provide a mobile X-ray unit that has visual information regarding the full geometry of the X-ray beam emitted from an exit surface of the X-ray tube. To this end, the mobile X-ray unit, according to the present disclosure, includes an indicator configured to delineate at least a portion of the X-ray beam emitted from the exit surface of an X-ray tube.

It will be appreciated that the terms 'mobile' and 'portable' in the context of the present application may be interchangeable as these terms equally relate to an easily moved or transported device, such as, for example, a device which may be moved or transported by a single individual.

Treatment efficacy may be substantially improved when an indicator is provided for delineating at least a portion of the generated X-ray beam, like a central axis thereof, and/or a partial or a full beam geometry. In an exemplary embodiment, the indicator is a light source. The light source may be arranged to provide a shadow-like indication of a two-dimensional area irradiated by the X-ray beam (full or partial). In other embodiments, the light source may be advantageously arranged to provide a light beam which illuminates either partially or wholly an area of the surface irradiated by the X-ray beam. In this manner, the target region on the skin and the X-ray beam may be properly aligned.

The light source may be arranged in the X-ray applicator or, alternatively, the light source may be arranged around an outer surface of the X-ray applicator. When the light source is arranged in the X-ray applicator, the light source may be configured to delineate the central axis of the X-ray beam and/or the full beam geometry. When the light source is arranged around the outer surface of the X-ray applicator, the light source may be arranged to delineate a central axis of the X-ray beam, preferably at a pre-determined distance from the X-ray applicator. This may be advantageous when the X-ray applicator is used at a standard distance from the patient's skin. However, it will be appreciated that the light source arranged around the X-ray applicator may be adjusted so as to indicate the central axis of the X-ray beam at a variety of axial distances from the X-ray applicator.

It will be appreciated that the light source may be arranged to provide a contrast image of at least a portion of the X-ray beam. For example, the light source may be arranged to generate a light image of a portion of the X-ray beam. The light image may be surrounded by a darker background. Alternatively, the light source may be arranged to generate a shadow image. The darker image of the portion of the X-ray beam may be surrounded by a lighter background. In both cases, the contrast edge of the image may be used for suitably aligning the X-ray applicator and the target region.

In various embodiments, the indicator includes an array of light sources concentrically arranged around the X-ray applicator. Although it may be sufficient to provide a single light source that generates a narrow beam for indicating the central axis of the X-ray beam, it may be advantageous to provide a plurality of light sources each of which generates a narrow light beam. These light beams may intersect at a given distance from the lower surface of the X-ray applicator. In this manner, the X-ray applicator may be positioned at a prescribed distance from the skin. In order to ensure a correct coverage of the target region by the X-ray beam, the X-ray applicator may be positioned so that the indicated center of the X-ray beam is positioned substantially at a center of the target region. It will be appreciated that these embodiments function particularly well for regular shaped X-ray beams, for example, when a circular, a square, an elliptic, or a triangular collimator is used for shaping the X-ray beam.

In various embodiments, the light source may be disposed inside the X-ray applicator for generating a light beam configured to be intercepted by the collimator for providing a light image of the X-ray field emitted from the exit surface.

This embodiment may be advantageous when the full shape of the X-ray beam is to be delineated such as, for example, in situations when an irregular beam shape is used. In such cases, the light source may be provided near the target region or, via a mirror, off-axis, for generating a light beam configured to be intercepted by the collimator. It will be appreciated that a direction of propagation of the light beam must essentially conform to a direction of propagation of the X-ray beam. In one embodiment, when a mirror is used, the light source may advantageously be positioned off-axis minimizing its radiation damage.

In various embodiments, the indicator includes a light source and an optical fiber configured to deliver light from the light source for interception by the collimator.

The light source may be positioned outside the X-ray applicator so as to minimize the size of the X-ray applicator. For example, the light source may be arranged in the base of the X-ray unit and the optical fibers may run from the base to the X-ray applicator for illuminating the collimator and for obtaining an image of the generated X-ray beam.

The indicator may include a plurality of optical fibers distributed in the X-ray applicator in an area above the collimator for illuminating a collimator opening and for causing the collimator opening to intercept the resulting light field. This embodiment may be advantageous for obtaining a light field having a substantial intensity.

In various embodiments, the light source may emit a narrow light beam arranged inside the applicator for delineating the longitudinal axis of the X-ray beam. In some embodiments, a miniature laser source may be used.

In various embodiments, the collimator may be provided with automatic identification devices configured to generate a signal in the control unit representative of collimator characteristics.

It may be advantageous to automatically identify when the collimator has been inserted in the X-ray tube so as to minimize or eliminate human errors in defining the field geometry. For example, the collimator may be positioned in a receptacle having a resistive path whose resistivity may be changed. The collimator may be arranged with projections adapted to cooperate with the resistive path of the receptacle for changing the resistivity of the receptacle, and thus, generating a signal indicating that the collimator has been inserted into the receptacle. In some embodiments, the signal may be transmitted to the control unit of the mobile X-ray unit for independent verification. It is contemplated that the mobile X-ray unit includes a set of collimators each having identification devices.

In various embodiments of the present disclosure, the mobile X-ray unit may include a signaling device configured to indicate that an X-ray beam has been generated.

It may be advantageous to provide a signaling device that indicates the operational state of the X-ray beam. For example, the signaling device may be a light on the X-ray applicator. One or more light emitting diodes may be used for this purpose. It may be possible to provide a plurality of signaling devices that indicate the energy of the generated X-ray beam.

For example, for the X-ray beam of a lower portion of the spectrum (about 50 kV), a first indicator may be used, such as, for example, a first light color. For an intermediate portion of the spectrum (about 60-65 kV), a second indicator may be used, such as, for example, a second light color. Finally, for the higher portion of the spectrum (66-75 kV, preferably 66-70 kV), a third indicator may be used, such as, for example, a third light color. It will be appreciated that a plurality of possibilities exist for indicating different spectra, including but not limited to a progressive illumination of a plurality of indicators upon hardening of the delivered X-ray beam. It will be further appreciated that such indication of the kV range may be disposed in the device, in a user interface, or in a supplementary unit. It will be further appreciated that the named kV ranges may be scaled with, for example the factors 1:1; 1:2; 1:3; 1:4; 1:5. Preferably, the signaling devices comprise a light indicator arranged on an outer housing. The arrangement of the signaling devices is advantageous as the patient is made aware about the starting point and the termination of irradiation so that the patient may retain a static position during the course of treatment. It will be appreciated that the signal device that indicates that the X-ray beam is on is separate from the indicator configured to delineate the X-ray beam discussed above.

In various embodiments of the present disclosure, the mobile X-ray unit may include a cooler arranged with piping to provide a cooling medium in a vicinity of the X-ray tube. The piping may run in a space between the X-ray tube and a shielding wall associated with the X-ray tube.

It may be advantageous to provide a space between the outer surface of the X-ray tube and the inner surface of the X-ray tube, that is at least partially filled with a coolant. In some embodiments, it may be advantageous to provide circulated water as a cooling agent due to high specific heat capacity, offering improved heat transfer of water with respect to a gas. However, pressurized gas may also be used as a suitable coolant. In some embodiments, a temperature sensor may be arranged on the outer housing of the X-ray applicator for measuring actual temperature of the outer housing. The temperature sensor may be connected to the control unit for controlling the cooler and/or for controlling the high voltage supply. Should the temperature rise above a pre-determined shut-off value, the control unit may be arranged to disable the high voltage supply and/or to intensify the cooling mode, for example, by increasing a pumping capacity of the coolant.

In various embodiments of the present disclosure, a radiation detector may be provided inside the outer housing for detecting the X-ray beam.

It may be advantageous to provide an independent radiation detector for detecting the presence of the generated X-ray beam. In some embodiments, the mobile X-ray unit includes a primary timer which sets a time for the high voltage supply for delivering a predetermined radiation dose. The radiation sensor accommodated inside the outer housing of the X-ray applicator may be part of a secondary timer circuit adapted to shut down the high voltage supply after the predetermined radiation dose is delivered. In this way radiation safety control may be improved.

In various embodiments of the present disclosure, the X-ray applicator may include an exit surface directed towards a patient. The surface may be covered by an applicator cap.

It may be advantageous to provide an applicator cap, which may have many functions in use. In one example, the applicator cap may be used for protecting the exit surface of the X-ray applicator from intra-patient contamination. In another example, the thickness of the cap in a direction of the beam propagation may be sufficient for substantially eliminating electron contamination from the X-ray beam. In some embodiments, the applicator cap may be manufactured from PVDF (Polyvinylidene fluoride) and may have a thickness of about 0.4-0.7 mm, preferably 0.6 mm, across the window portion. The applicator cap may have a density of about 1.75-1.8, and preferably 1.78. In other embodiments, the applicator cap may have a thickness of 0.3-0.6 mm, and preferably 0.5 mm, across the window portion. In these embodiments, the applicator cap may have a density of 1.30-1.45, and preferably 1.39, and may be manufactured from PPSU (polyphenylsulfone). It is found that these materials may be particularly suitable as they as stable under influence of the X-rays and are suitable for different types of sterilization procedures, such as chemical sterilization, or sterilization under elevated temperatures. It will be appreciated that those skilled in the art will readily appreciate the relationship between the energy of the secondary electrons emanating from the X-ray tube and a required thickness of a given material, such as, for example plastic, glass, ceramics, sufficient for fully intercepting these electrons. In some embodiments, the applicator cap may be disposable.

In yet another example, the applicator cap may function as a heat absorber to dissipate the elevated temperature of the X-ray applicator. As a result the patient will feel the applicator contacting the skin as a slightly warm object.

It will be appreciated that the indicator configured to delineate the X-ray beam may be configured to have sufficient intensity to provide a field image through the applicator cap. Lasers may be particularly suited for this purpose. Alternatively, light emitting diodes may be used. In another embodiment, an arrangement of one or more light sources generating a narrow beam outside the X-ray applicator may be advantageous. In that embodiment, one or more sources may be arranged on respective support arm such that the respective narrow light beams are not intercepted by the applicator cap.

In various embodiments, the X-ray applicator may be connected to the base using a displaceable panel. The flexible cabling may run substantially in the displaceable panel.

It may be advantageous to provide an intermediate mechanical unit connecting the base of the mobile X-ray unit and the X-ray applicator, and for housing the flexible cables so as to prevent the cables from entangling. The displaceable panel may be arranged with a pre-defined travel distance with respect to a lowest achievable stand position and a highest achievable stand position. This may be advantageous for increasing durability of the cables tubes and wiring of the mobile X-ray unit, and especially of the tubes accommodating the coolant.

It may be advantageous to provide the remote light source as is discussed above in the displaceable panel as this may reduce the required length of the optical fibers.

In various embodiments, the displaceable panel may include a user interface for controlling the X-ray unit. In some embodiments, the user interface may be a display. For example, the display may be implemented as a touch screen arranged for enabling data input. Alternatively, the display may be arranged for echoing data. In this embodiment, the display may include buttons or other suitable means for entering input data into the mobile X-ray unit.

Another embodiment of the present disclosure is directed a method for visually delineating an X-ray beam emitted from a mobile X-ray unit. The mobile X-ray unit may include a base having a control unit and a power supply. The mobile X-ray unit may further include an articulated arm coupled to an X-ray applicator having an X-ray tube. The X-ray tube may include a target, a collimator, and an exit surface through which the X-ray beam may pass. The method may include generating an X-ray beam and shaping the X-ray beam. The method may further include providing a visual indication of at least a portion of the X-ray beam emitted from the exit surface.

In some embodiments, the target and the collimator are accommodated in a substantially cylindrically shaped outer housing, and a direction of propagation of the generated X-ray beam may be substantially parallel to the longitudinal axis.

Additional objects and advantages of the invention will be set forth in part in the description which follows, and in part will be obvious from the description, or may be learned by practice of the invention. The objects and advantages of the invention will be realized and attained by means of the elements and combinations particularly pointed out in the appended claims.

It is to be understood that both the foregoing general description and the following detailed description are exemplary and explanatory only and are not restrictive of the invention, as claimed.

The accompanying drawings, which are incorporated in and constitute a part of this specification, illustrate several embodiments of the invention and together with the description, serve to explain the principles of the invention.

BRIEF DESCRIPTION OF THE DRAWINGS

FIG. 3b presents a cross-sectional view of an X-ray applicator of the mobile X-ray unit having an indicator, according to a second embodiment of the present disclosure.

FIG. 3c presents a cross-sectional view of an X-ray applicator of the mobile X-ray unit having an indicator, according to a third embodiment of the present disclosure.

FIG. 8, E-E presents a cross-section along line VII-E of the X-ray tube of FIG. 8, according to embodiments of the present disclosure.

FIG. 8, F-F presents a cross-section along line VII-F of the X-ray tube of FIG. 8, according to embodiments of the present disclosure.

DESCRIPTION OF THE EMBODIMENTS

Reference will now be made in detail to the present exemplary embodiments of the invention, an examples of which is are illustrated in the accompanying drawings. Wherever possible, the same reference numbers will be used throughout the drawings to refer to the same or like parts.

Figure 1B:
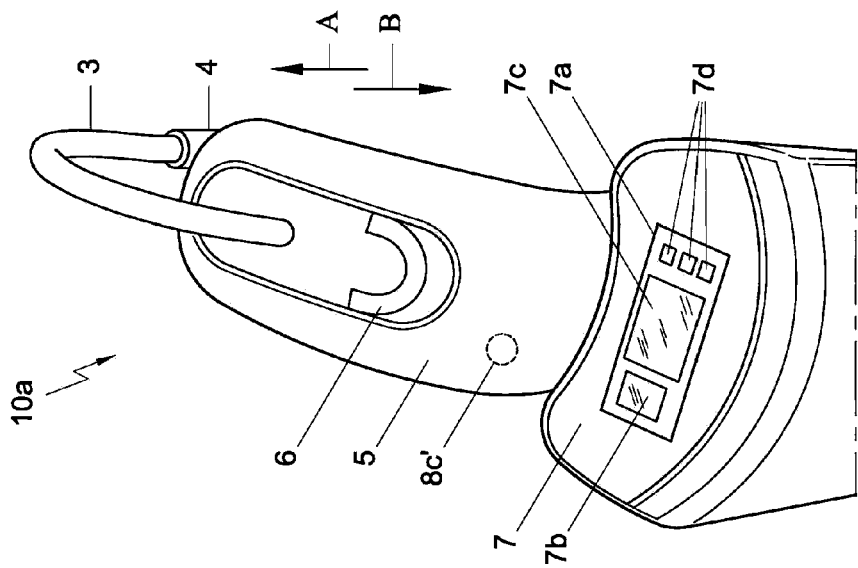
FIG. 1b a partial perspective view of a mobile X-ray unit illustrating movement of a displaceable panel, according to embodiments of the present disclosure.
Figure 1A:
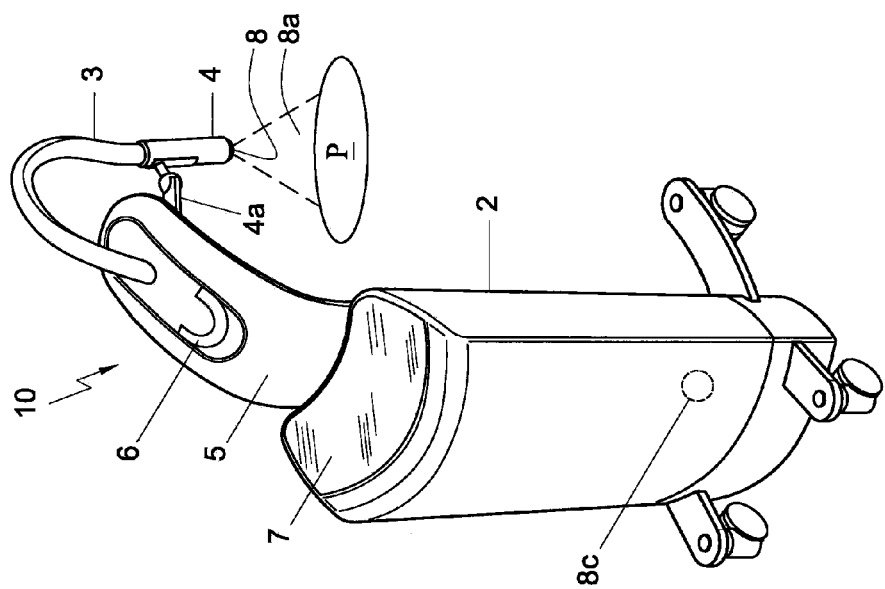
FIG. 1a presents a perspective view of a mobile X-ray unit, according to embodiments of the present disclosure.

FIG. 1a presents a partial perspective view of a mobile X-ray unit according to the invention. The mobile X-ray unit 10 comprises a base 2 having at least a high voltage supply unit, a cooling system, and a control unit (FIG. 2) for controlling an operation of an X-ray applicator 4. The X-ray applicator 4 includes an X-ray tube (FIG. 3) disposed in an outer housing of the X-ray applicator 4. The X-ray applicator 4 may be connected to the base 2 using flexible cables 3, which may be at least partially disposed in a displaceable panel 5. The X-ray applicator 4 may be coupled to an articulated arm 4a, which may include a pivot for varying the position of the X-ray applicator 4 in space. In some embodiments, the articulated arm 4a includes a brake (not shown) for holding the X-ray applicator 4 in a particular position in space. In one embodiment, the brake may be manually controlled and may be used for simultaneously switching on a light source used for aligning the X-ray applicator 4 with respect to a target region on a patient P.

The X-ray applicator 4 may include a longitudinal axis and an exit window 8 through which the generated X-ray beam exits the X-ray applicator 4. In some embodiments, the X-ray applicator 4 and the X-ray tube (not shown) are coaxial. In this manner, the X-ray beam 8a may propagate from the exit window 8 and may have a beam axis (not shown) that substantially corresponds to the longitudinal axis of the X-ray tube.

The X-ray applicator 4 may include an indicator. The indicator may provide a visual indication of at least a portion of the X-ray beam 8a on the patient P, when the X-ray applicator 4 is being positioned relative to the patient P. In an exemplary embodiment, the indicator may be a light source 8c. In some embodiments, the light source 8c may be disposed either inside the X-ray applicator 4 or around the X-ray applicator 4. In other embodiments, the light source 8c may be remotely positioned, for example in the base 2. In the latter case, light from the light source 8c may be conducted towards the X-ray applicator 4 using one or more optical fibers.

The articulated arm 4a may be mechanically connected to the displaceable panel 5. The displaceable panel 5 may be configured to move relative to the base 2 to alter a vertical position of the X-ray applicator 4. In some embodiments, the displaceable panel 5 may be provided with a handle 6 enabling easy manipulation thereof. The displaceable panel 5 may be guided along suitable rails for enabling a substantially smooth and shock-free displacement thereof.

The displaceable panel 5 may include a display 7, which may function as a suitable user interface 7a. For example, patient data, such as, for example, a photo of the patient and/or a photo of a lesion, may be provided in window 7b, whereby relevant patient information, such as the date of birth, gender, dose prescription and dose delivery protocol and so on may be displayed in window 7c. Inputs 7d may also be provided. Alternatively and/or additionally, suitable hardware switches or buttons may be provided as well. The display panel 7 may also include a button, switch, or other structure to activate the light indicator. Alternatively, the light source 8c may always be on when the X-ray unit is switched on.

FIG. 1b presents a partial perspective view of the mobile X-ray unit illustrating movement of the displaceable panel. In this enlarged view 10a, specific elements of the displaceable panel 5 are depicted. A handle 6 may be implemented as a mechanical item for pulling or pushing the displaceable panel 5. Alternatively, the handle 6 may be arranged as an electrical actuator for triggering motors (not shown) for displacing the displaceable panel 5. For example, when the handle 6 is pulled the motors may be activated for causing the panel 5 to displace in a direction A. Pushing of the handle 6 may cause lowering of the panel 5 in a direction B. In some embodiments, the mobile X-ray unit 10 includes stops, limits, or other known structures for limiting the movement of the displaceable panel 5. This may be advantageous for ensuring mechanical stability of the mobile X-ray unit 10 (limitation of the upper level) and may also be beneficial for preventing cable damage (limitation of the lower level). In some embodiments, the displaceable panel 5 may travel along built-in rails whose length may be chosen for limiting the displacement range of the panel 5 in a desirable way.

In one exemplary embodiment, a light source 8c' configured to delineate at least a portion of the X-ray beam, may be positioned inside the displaceable panel 5. Suitable optical fibers (not shown) may be used for conducting light from the light source 8c' towards the X-ray applicator. More details on suitable light source arrangements, although not limitative, are discussed with reference to FIGS. 3a-3c.

Figure 1C:
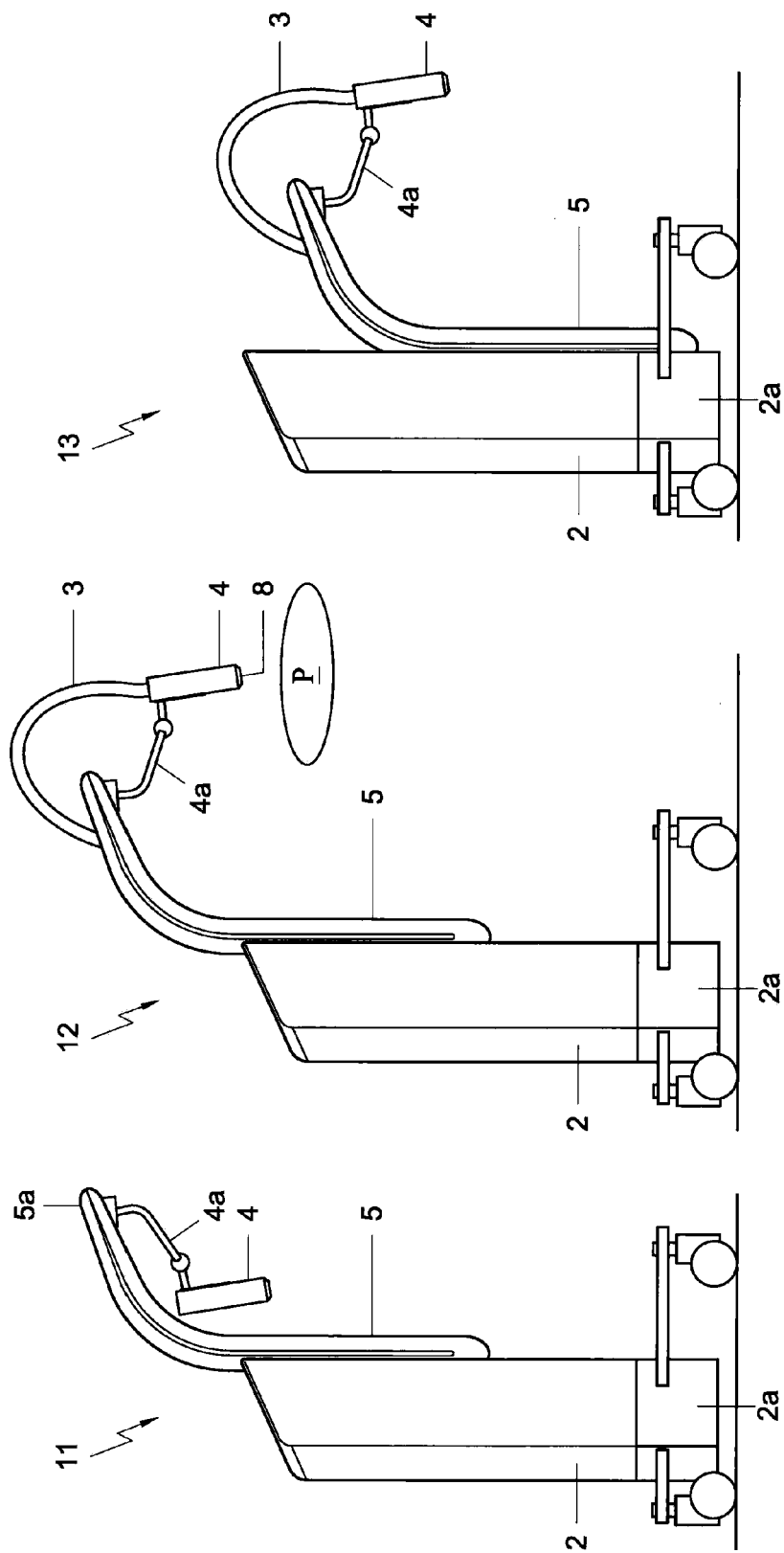
FIG. 1c presents a schematic view of the mobile X-ray unit shown in FIGS. 1a and 1b, illustrating displacement of an X-ray applicator of the X-ray unit relative to a base of the mobile X-ray unit, according to embodiments of the present disclosure.

FIG. 1c illustrates the displacement of the X-ray applicator 4 of the X-ray unit 10. It will be understood that the mobile X-ray unit 10 may be configured so as to support a broad range of translational and rotational movements of the X-ray applicator 4.

In view 11, the X-ray applicator 4 is in its retracted position. It will be appreciated that cabling is not depicted for clarity reasons. The retracted position may be suitable for transport of the mobile X-ray unit 10 towards a booth and/or for maneuvering the X-ray unit 10 around the patient. In order to retract the X-ray applicator 4 as close as possible to the base 2, the articulated arm 4a may be positioned under the outer portion 5a of the displaceable panel 5. For ensuring stability of the mobile X-ray unit 10 during maneuvering thereof, a load block 2a may be provided for lowering the point of gravity of the X-ray unit 10.

In view 12, the X-ray applicator 4 may be in an extended position having an X-ray exit surface 8 oriented towards a patient P. In order to suitably position the X-ray applicator 4 with respect to the patient P, the displaceable panel 5 may be moved to an intermediate position located between the lowest position and the highest position of the displaceable panel 5. The articulated arm 4a may be used for suitably rotating the X-ray applicator 4 about a rotation axis. Preferably, a rotation axis is selected to coincide with a direction of emanation of the X-ray beam from the exit surface 8 for a vertically oriented X-ray applicator 4.

In view 13, the X-ray applicator 4 may be in a lowered position. For this purpose the displaceable panel 5 may be in its lowest position and the arm 4a may be used for orienting the X-ray applicator 4 in a desirable way.

Figure 2:
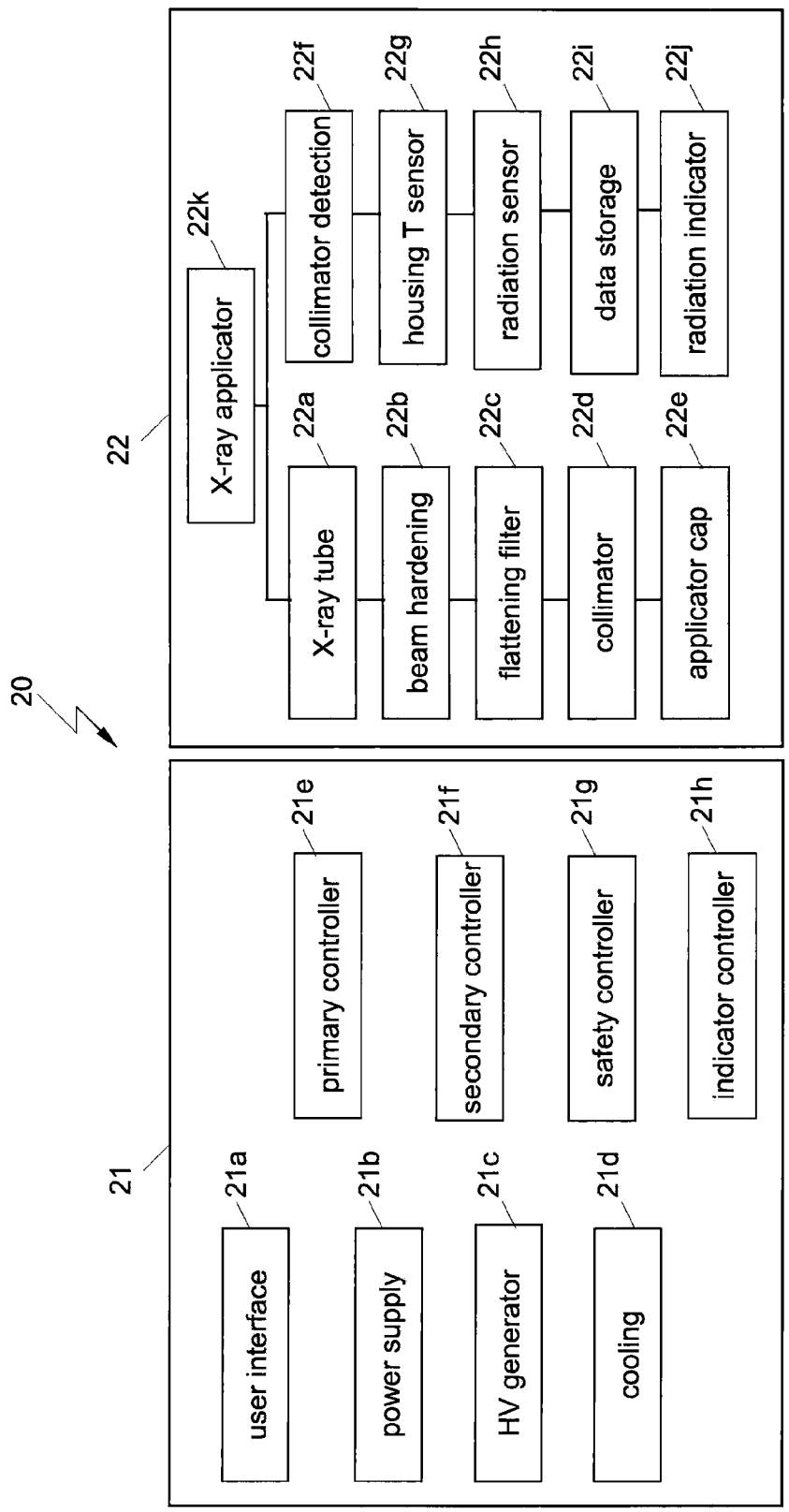
FIG. 2 presents a diagrammatic representation of the mobile X-ray unit, according to embodiments of the present disclosure.

FIG. 2 is a diagrammatic representation of the mobile X-ray unit 10 according to the invention. The mobile X-ray unit 10 according to the invention comprises a high voltage supply, preferably adapted to generate 50-75 kV X-rays in a suitable X-ray tube, a cooling system for cooling the X-ray tube during use, and a control system for controlling electronic and electric parameters of sub-units of the X-ray unit during use. View 20 diagrammatically depicts main units of the control system 21 and of the X-ray applicator 22.

The control system 21 includes a hard wired user interface 21a for enabling switching on and switching off of the high voltage supply 21b. In some embodiments, the high voltage supply 21b comprises a high voltage generator 21c with improved ramp-up and ramp-down characteristics. The high voltage supply is preferably operable for delivering power of about 200 W in use. In some embodiments, the ramp-up time may be of the order of 100 ms. The hard wired interface 21a, may also be arranged to automatically switch on the cooling system 21d when the high voltage generator is switched on. In addition, the control system 21 may include a primary controller 21e arranged for controlling the dose delivery from the X-ray applicator 22 in use. The primary controller 21e may be provided with a primary counter adapted to register time lapsed after the X-ray radiation is initiated. The primary counter may then automatically switch off the high voltage supply to the X-ray tube 22a in the event a pre-determined dose is reached. It will be appreciated that the pre-determined dose is at least dependent on the energy of the X-rays and the dose rate, which may be calibrated in advance. Where calibrated data is made available to the primary controller, adequate primary dose delivery control may be achieved. In some embodiments, a secondary controller 21f may be provided for enabling an independent loop of dose delivery control. The secondary controller 21f may be connected to a dose meter accommodated inside the X-ray applicator 22 in the X-ray field before the collimator 22d. Accordingly, the dose meter may provide real-time data on actual dose delivery taking into account dose variation during ramp up and ramp down of the high voltage source. Still preferably, the control system 21 may include a safety controller 21g adapted to compare readings from the primary controller 21e and the secondary controller 21g for switching off the high voltage generator 21c after a desired dose is delivered. Additionally and/or alternatively, the safety controller 21g may be wired to guard emergency stop, door interlock and a generator interlock.

The control system 21 may further include an indicator controller 21h for controlling source light source configured to delineate at least a portion of an X-ray beam. The indicator controller 21h may be linked to a power supply unit 21b for switching on the light source once the system 21 is on. In some embodiments, the light source may be switched on demand. Accordingly, the indicator control 21h may be arranged to provide electrical power to the light source when triggered by the user. The user may provide trigger signal via a user interface, or, for example, using a dedicated hardware switch.

In an exemplary embodiment, the X-ray applicator 22 may include an X-ray tube 22a housed in an outer housing (shielding) 22k. The X-ray tube 22a may have a target-collimator distance of between 4 and 10 cm, and preferably 5 and 6 cm. The X-ray applicator 22 may further comprise a beam hardening filter 22b selected to intercept low-energy radiation and a beam flattening filter 22c, designed to intercept portions of X-ray radiation for generating a substantially flat beam profile near the exit surface of the X-ray applicator 22. Further, the X-ray applicator 22 may comprise one or more collimators 22d arranged to define treatment beam geometry. Preferably a set of collimators 22d may be used having, for example, diameters of 1, 1.5, 2, 2.5, 3, 3.5, 4, 4.5, 5 cm. It will be appreciated that although circular collimators are discussed, collimators of any shape, such as square, elliptic or custom made collimators are possible. It may be advantageous to have an X-ray applicator 22 with automatic collimator detection means 22f adapted to automatically signal which collimator is being used. In some embodiments, resistive sensing may be used to identify which collimator 22d is being used. In particular, each collimator may be provided with at least a couple of projections for bridging a resistive path provided in a collimator receptacle. The resulting electrical resistance of the receptacle constitutes a signal representative of a collimator being used.

The X-ray applicator 22 may also include a built-in temperature sensor 22g adapted to signal temperature of the X-ray tube 22a and/or its shielding 22k. The signal from the temperature sensor 22g may be received by the control system 21 which may carry out the analysis thereof. Should the measured temperature be elevated beyond an allowable level, an alarm signal may be generated. Optionally, a shut-off signal to the high voltage generator may be provided. The X-ray applicator 22 may further comprises a radiation sensor 22h arranged inside the outer housing 22k for detecting X-ray radiation which may be delivered by the X-ray tube 22a. Preferably, for safety reasons the X-ray applicator 22 may include a non-volatile data storage 22i arranged for recording operational parameters at least of the X-ray tube 22a. Further, to enhance radiation safety, the X-ray applicator 22 may be provided with a radiation indicator 22j arranged for providing a visual and/or an audio output to the user and/or the patient regarding ON/OFF condition of the X-ray tube 22a. It will be appreciated that the radiation indicator 22j may comprise a plurality of signaling devices. In one embodiment, at least one signaling device, for example a light emitting diode (LED), is associated with the X-ray applicator 22 and provided on the X-ray applicator 22. It is understood, however, that the signaling devices may be positioned at any other location on the mobile X-ray unit.

Figure 3A:
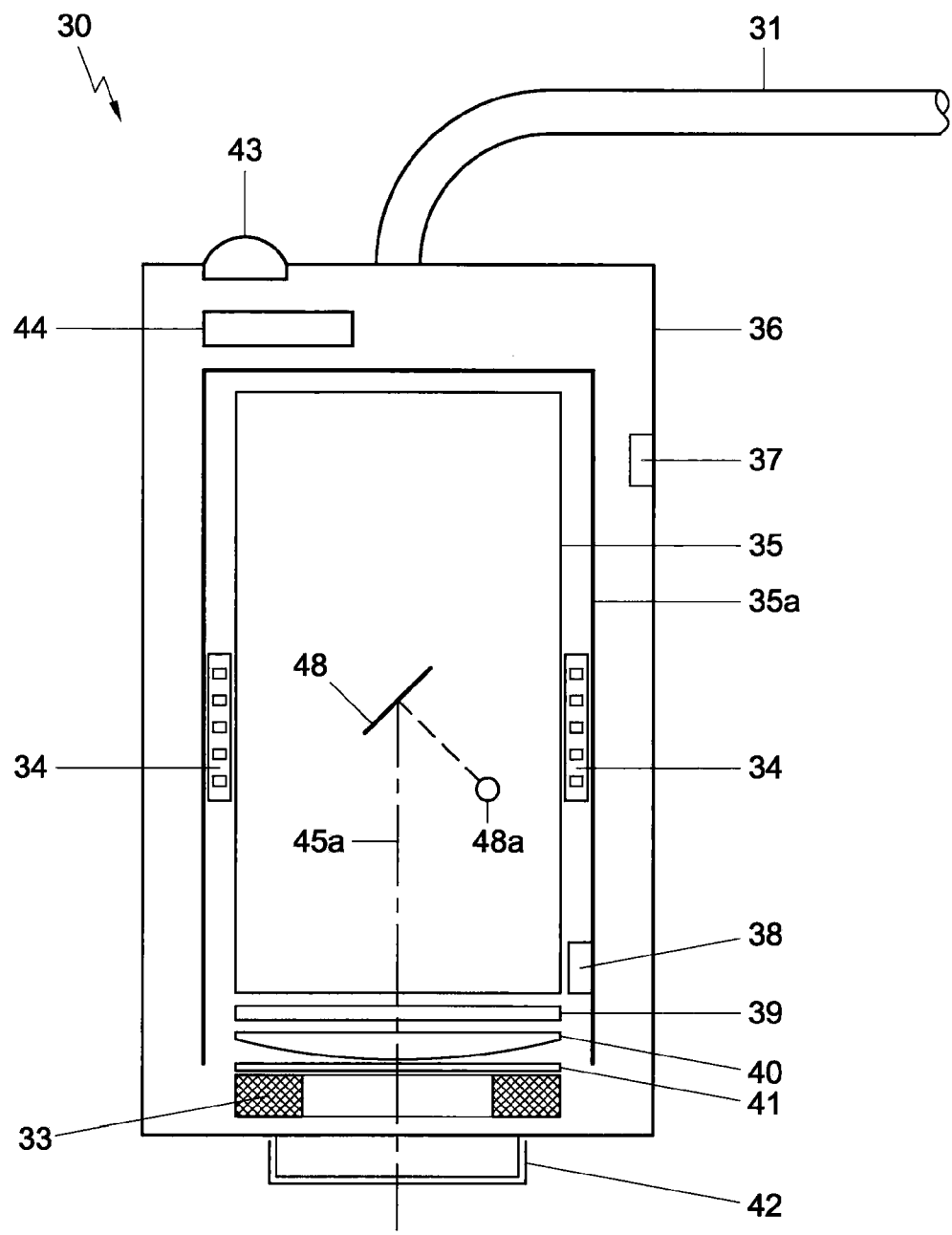
FIG. 3a presents a cross-sectional view of an X-ray applicator of the mobile X-ray unit having an indicator, according to a first embodiment of the present disclosure.

FIG. 3a presents a cross-section of an X-ray applicator of the mobile X-ray unit having an indicator in accordance with a first embodiment of the present disclosure. The X-ray applicator 30 includes an outer housing 36 and an X-ray tube 35 disposed in the outer housing 36. The X-ray tube 35 may have an external shielding 35a, a target (not shown), and a collimator 33.

In one embodiment, the indicator may be light source 48a. The light source 48 may cooperating with a mirror 48 for emitting a light beam indicative of a two-dimensional beam of X-rays produced by the X-ray tube 35. In some embodiments, X-rays have a propagation axis 45a which coincides with a longitudinal axis of the X-ray tube 35. The light source 48a and the mirror 48 may be arranged so that the light beam may substantially propagate along the longitudinal axis of the X-ray tube 45a.

When the light beam is intercepted by the collimator 33 a visual indication and simulation of the two-dimensional X-ray beam is created so as to facilitate alignment of the X-ray applicator and the target region of the patient P.

In one embodiment, the distance between a target of the anode (not shown) and the collimator 33 is in the range of 4 to 10 cm, preferably about 5 to 6 cm. Such relatively short target-collimator distance may generate an X-ray beam having a substantially narrow penumbra (1.5-1.8 mm for 20/80% lines) and good beam flatness due to a relatively small focal size. It will be appreciated that while the anode has a longitudinal axis arranged substantially parallel to the longitudinal axis 45a of the X-ray tube 35, the target may be a substantially flat plate which extends substantially perpendicular to the axis 45a.

The X-ray applicator 30 further include a filter 39 for hardening the X-ray beam emanating from the target, a beam flattening filter 40 for flattening out a beam profile, and a collimator receptacle 41 for receiving collimator 33.

A cooling system 34 may be provided so as to prevent overheating of the X-ray tube 35. In one embodiment, the cooling system 34 may be arranged in the space between the X-ray tube 35 and the shielding 35a in contact with the surface of the X-ray tube 35. A suitable coolant may be provided using a pipe 31. It is contemplated that the coolant may be water, a pressurized gas, or even a special oil. The X-ray applicator 30 may further comprise a temperature sensor 37.

The X-ray assembly 30 may further include a suitable radiation detector 38 connected to a radiation indicator 43. Data collected by the radiation detector 38 may be stored in a data storage unit 44.

In order to protect an X-ray exit surface of the X-ray applicator 30 from intra-patient contamination, an applicator cap 42 may be provided to cover at least the exit surface of the X-ray applicator 30. In some embodiments, the applicator cap 42 is thick enough to fully intercept secondary electrons emanating from the X-ray applicator. The applicator cap 32 may be manufactured from PVDF (polyvinylidene fluoride) and may be about 0.4-0.7 mm, and preferably 0.6 mm thick across the window portion. The applicator cap may have density of about 1.75-1.8, and preferably 1.78. Alternatively the applicator cap 42 may be 0.3-0.6 mm thick, and preferably 0.5 mm thick across the window portion. In those embodiments, the applicator cap 32 may have a density of 1.30-1.45, and preferably 1.39. Further, the applicator cap 42 may be manufactured from PPSU (polyphenylsulfone). These materials may be particularly suitable as they as stable under influence of the X-rays and are suitable for different types of sterilization procedures, such as chemical sterilization, or sterilization under elevated temperatures.

FIG. 3b presents a cross-section of an X-ray applicator of the mobile X-ray unit having an indicator in accordance with a second embodiment of the present disclosure. In this exemplary embodiment, the indicator includes at least one optical fiber 47a connected to a light source that may be positioned remotely in, for example, base 2 (FIG. 1a).

An anode 45 may have a longitudinal axis coaxially arranged with respect to a longitudinal axis 45a of the X-ray applicator 30. Accordingly, a central axis of the X-ray beam emitted by the anode 45 substantially coincides with the longitudinal axis 45a of the X-ray applicator 30.

Optical fiber 47a may be provided in the collimator receptacle 41 above the collimator 33. The optical fiber 47a may be configured to generate a light field that is substantially centered about the collimator opening 33 for creating a two-dimensional cross-section of an X-ray beam emitted from the collimator 33. In this embodiment, optical fiber 47a may be configured to emit a substantially narrow beam having a divergence representative with expected divergence of the X-ray beam.

Alternatively, it may be possible to use the optical fiber 47a for visualizing a central axis 45a of the X-ray beam in addition to visualizing of the two-dimensional area of the X-ray beam. In this case the optical fiber is advantageously arranged to emit a narrow beam light producing a miniature light spot on a surface of the patient. In one embodiment, a dimension of the light spot is less than 5 mm$^2$, and more preferably a dimension of the light spot is about 1 mm$^2$. A suitable light emitting diode or a laser may be used for generating light emitted from the fiber 47a. In one embodiment, the light emitting diode and the laser are remotely arranged with respect to the X-ray applicator 30. It will be appreciated that an alternative configuration may be used such as for example, having one or more light sources that may be electrically connected to one or more optical fibers.

FIG. 3b presents a cross-section of an X-ray applicator 30 of the mobile X-ray unit having an indicator in accordance with a second embodiment of the present disclosure. In this exemplary embodiment, the indicator may be disposed externally of the X-ray applicator 30 and may be one or more light sources 52.

As illustrated in FIG. 3b, the X-ray applicator 30 may include an anode 45 provided with a target for generating an X-ray beam 45c having the longitudinal X-ray axis 45a. The one or more light source 52 may be configured to illuminate the longitudinal axis 45a of the X-ray beam 45c at a pre-determined distance D from the lower surface 49 of the X-ray applicator 30. It will be appreciated that the lower surface 49 may relate to the exit window as discussed with reference to FIG. 1a, or it may relate to the applicator cap, as will be discussed with reference to FIG. 4.

The one or more light sources 52a, 52b may be disposed on support arms 54a, 54b. Light sources 52a, 52b may generate narrow light beams 53a, 53b that may be directed towards the axis 45a and intersect at a pre-determined distance D from the lower surface 49 of the X-ray applicator 30. Preferably, the distance D is selected to be between 0.5 and 2 cm. The support arms 54a, 54b may be arranged so that light beams 53a, 53b do not intersect the X-ray applicator 30.

In use, a user may position the X-ray applicator 30 with respect to the patient P in such a way that the beams 53a, 53b intersect at the surface of the patient. However, should the treatment regime require the use of a dose build-up material, the beams 53a, 53b may cross on a surface of the dose build-up material. In some embodiments, the support arms 54a, 54b may be adjustable to indicate the central axis 45a at different distances from the lower surface 49 of the X-ray applicator 30.

In order to calibrate adjustment of the support arms, a transparent calibration phantom may be used, wherein the central axis and depth are marked. It will be appreciated that although FIGS. 3a-3c disclose separate embodiments of the indicator, combination of such embodiments is contemplated as well. For example, embodiments directed to indicating the central axis may be combined with embodiments directed to indicating the complete field. In addition, internal and external indicators may be combined.

Figure 4:
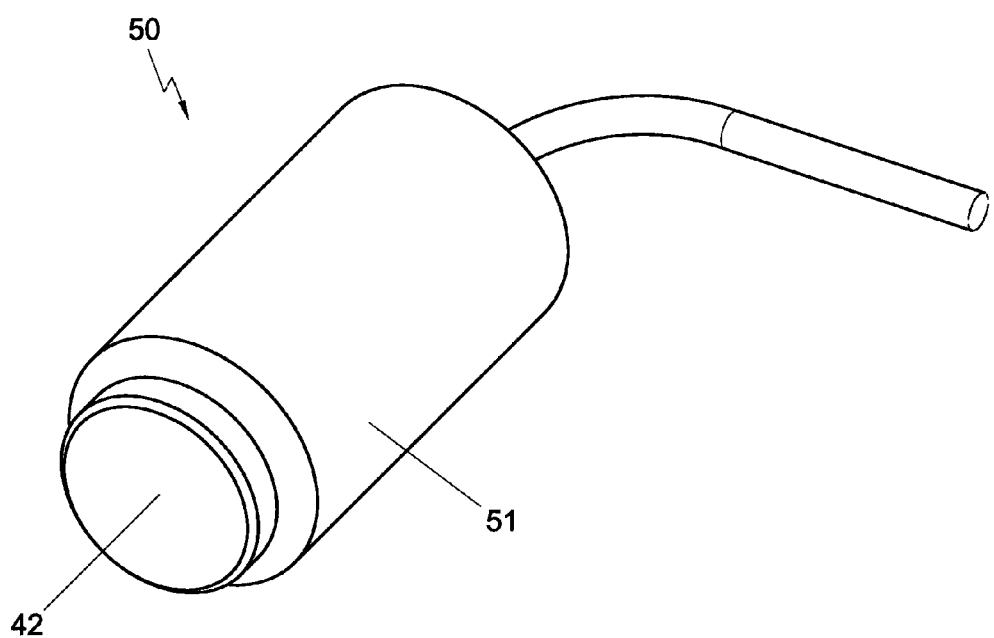
FIG. 4 presents a partial perspective view of the X-ray applicator provided with an applicator cap, according to embodiments of the present disclosure.

FIG. 4 presents a partial perspective view of the X-ray applicator provided with an applicator cap. The applicator cap 42 may be manufactured from transparent glass, transparent plastic, or from ceramics as well as from PVDF and PPSU. Applicator cap 42 may also be manufactured from a metal. In the latter case, the applicator cap may be sterilized, otherwise, the applicator cap 42 may be a disposable applicator cap. In view 50 of FIG. 4, it is seen that an outer dimension of the X-ray applicator 51 may be larger than the outer dimension of an exit portion covered by the applicator cap 42. Although such embodiment is preferable for minimizing total weight of the X-ray applicator 51, it may be possible that the exit portion has the same dimension as the body of the X-ray applicator 51.

Figure 5:
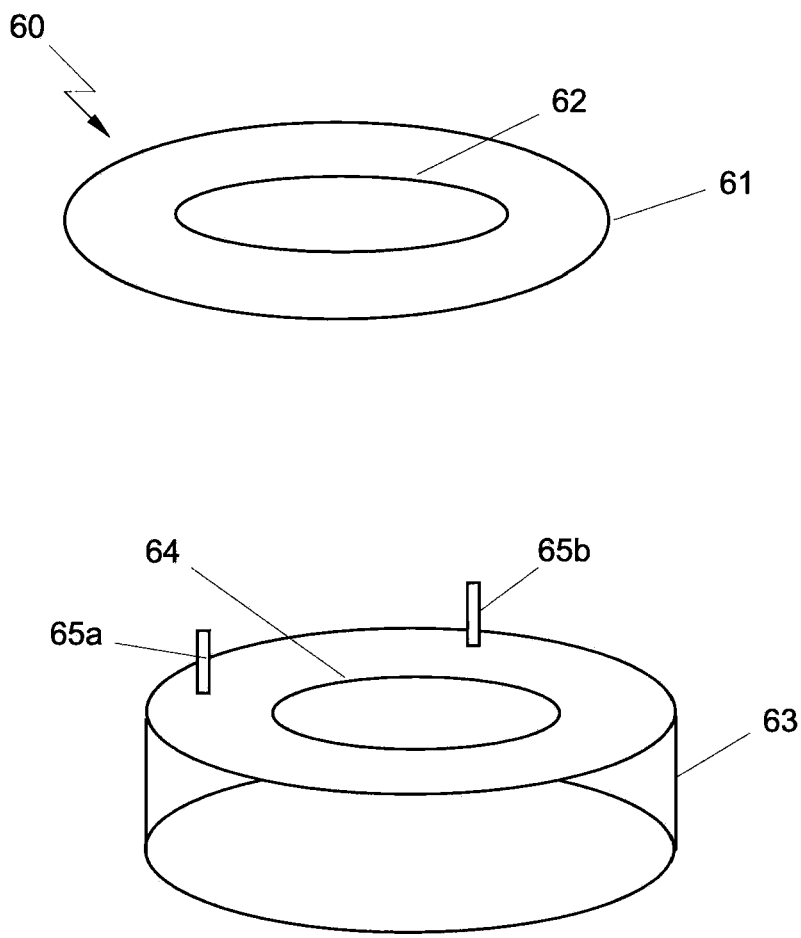
FIG. 5 presents a perspective view of a collimator provided with identification devices, according to embodiments of the present disclosure.

FIG. 5 presents a perspective view of a collimator with identification devices. The collimator 63 may be provided with a central opening 64 for defining a shape and dimension of the resulting X-ray beam emitted from the X-ray applicator 30 as is discussed with reference to FIGS. 3a-3c. The collimator 63 may be adapted to be fittingly received in a collimator receptacle 61. In order to enable automatic collimator identification, the collimator 63 may be provided with two projections 65a, 65b, adapted to interact with a resistive path 62 in the collimator receptacle 61. When the projections 65a, 65b come into contact with the path 62 a net resistance of the collimator receptacle 61 may be changed. The change in the resistance of the collimator receptacle 61 may be used to indicate when the collimator has been inserted in the collimator receptacle 61. It will be appreciated that for a set of collimators, each collimator may be provided with a unique pair of projections leading to a distinguishable change in the net resistivity of the collimator receptacle 61. Those skilled in the art will readily appreciate that a plurality of pairs 65a, 65b may be positioned at different locations on a surface of the collimator 63. Alternatively, it is possible to provide each collimator 63 with an electronic identification device such as, for example, a chip cooperating with a plug. When the plug is plugged-in the collimator receptacle 61 (provided with a cooperating socket), a signal may be transferred to the control unit of the mobile X-ray unit 10.

Figure 6:
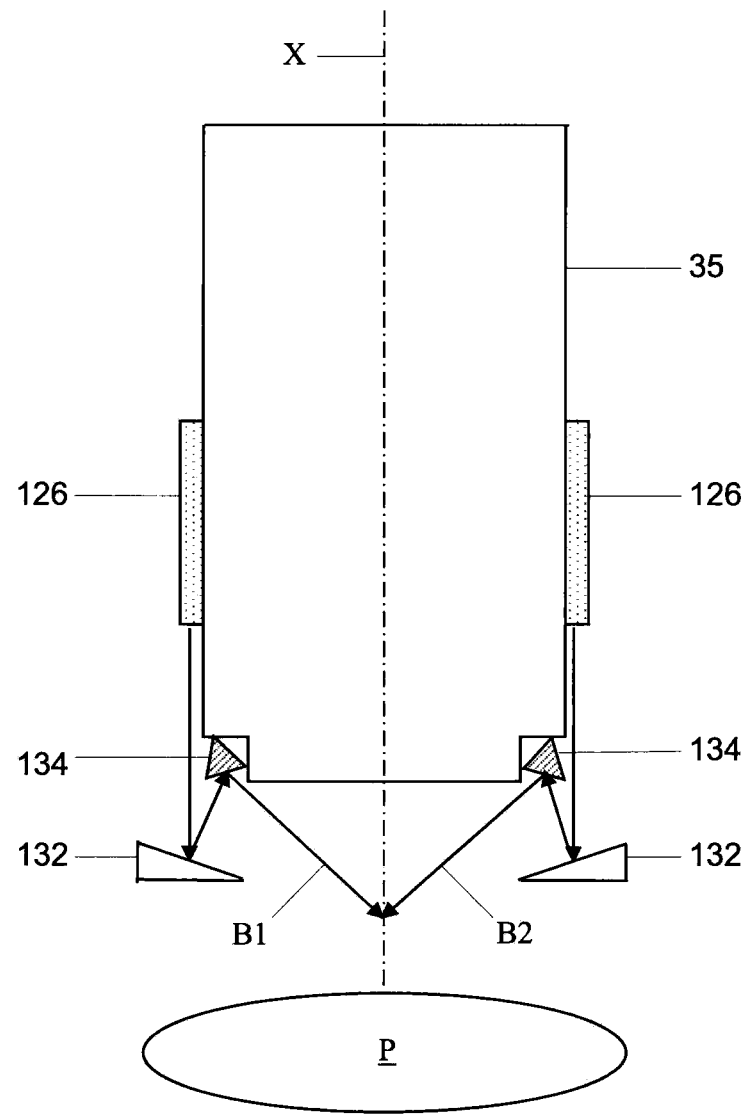
FIG. 6 presents a sectional view of the X-ray tube, according to embodiments of the disclosure.

FIG. 6 presents a schematic view of the indicator, in accordance with another embodiment of the present disclosure. In this embodiment, the indicator may be a light source 126 provided at a side surface of the X-ray tube 35. The light source may be an LED or any other suitable light source. Light emitted from the light source 126 may impinge on a reflective surface of the X-ray collimator 132. The light beam may then be reflected from a further reflective surface 134 and directed as respective beams B1 and B2 towards the central axis X of the X-ray tube 35. It will be appreciated that the X-ray tube 35 may be suitably shaped and manufactured for providing a reflective body 134. The reflective body 134 may be a concentric reflective ring attached in a corresponding recess of the X-ray tube 35. It will be further appreciated that the reflective surfaces 132 may be advantageously provided on a collimator surface facing away from the patient towards the X-ray source (not shown), positioned on the axis X. Those skilled in the art will readily appreciate how to arrange the collimator 134, and the X-ray tube 135, shown in FIG. 3 for enabling the geometry discussed in FIG. 6. A light spot generated by the light source 126 in the manner described above may be used for accurately positioning the X-ray tube 35 with respect to the patient P.

It will be further appreciated that the spatial position of the intersection between the beams B1 and B2 may be chosen to provide a minimum spot at a pre-determined distance from an outer surface of the X-ray applicator (not shown) accommodating the X-ray tube 35. For example, the pre-determined distance may be selected at 1, 2, 3, 4, or 5 cm from the outer surface of the X-ray applicator. In this way the alignment between the target region on the patient P and the central axis of the X-ray beam may be controlled and maintained. It may be advantageous to select the pre-determined distance at about 2-3 cm from the outer surface of the X-ray applicator for enabling maneuverability of the X-ray applicator without contacting the patient. When the X-ray applicator is set with respect to the patient P, using the articulated arm 4a, shown in FIG. 1a and the light source 126, may be positioned using fine mechanics. An embodiment of suitable fine mechanics is discussed with reference to FIG. 7.

It will be further appreciated that while the indicator (i.e., light sources) and the reflective bodies are explained with reference to the X-ray tube 35, it may be possible to implement a similar configuration attaching the light sources 126 to an outer surface of the X-ray applicator 4a, depicted in FIG. 1. In this case instead of using collimators for implementing a reflective purpose, a dedicated reflector may be used.

Figure 7A:
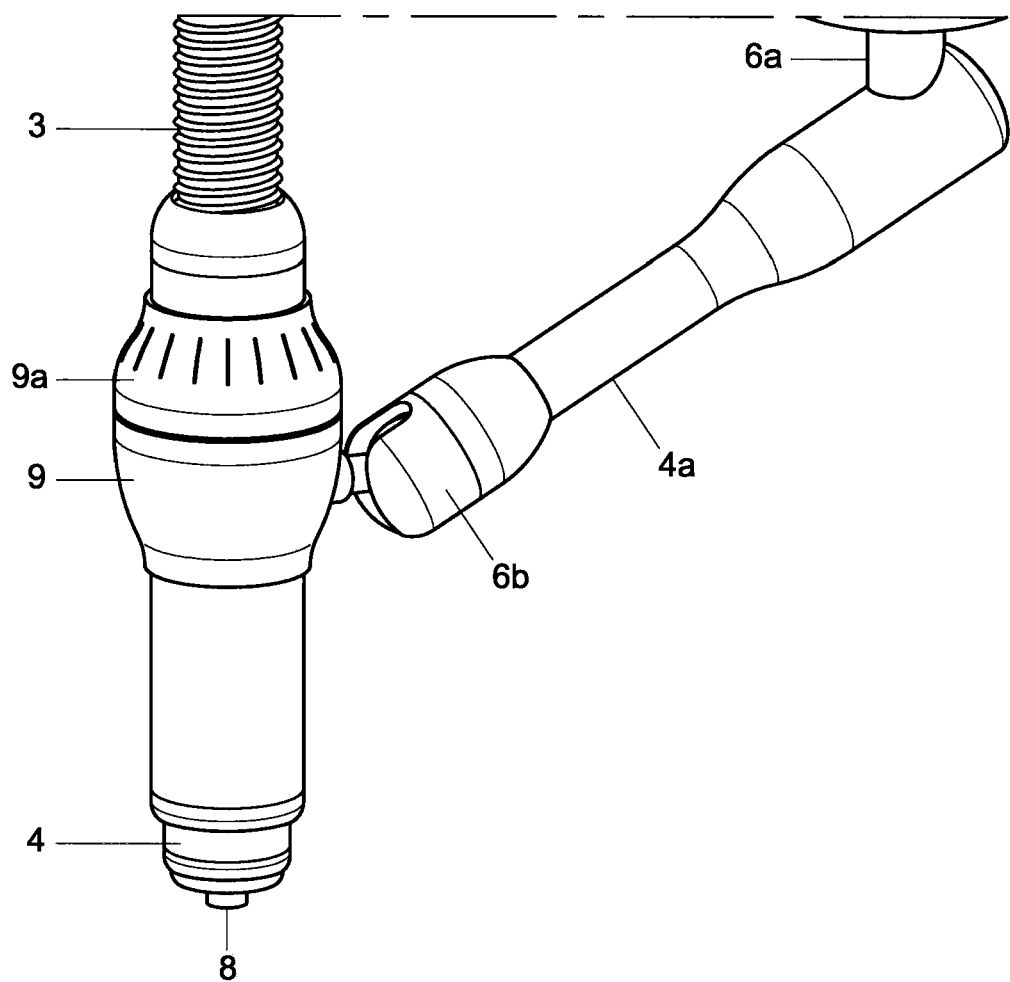
FIG. 7a presents a perspective view of a mechanism configured to finely adjust an axial position of the X-ray applicator, according to embodiments of the disclosure.

FIG. 7a presents a partial perspective view of a mechanism for finely adjusting an axial position of the X-ray applicator 4. In one embodiment, the X-ray applicator 4 may be provided in a sleeve 9 having a rotating portion 9a. The rotating portion 9a includes suitable mechanics engaged with the X-ray applicator 4 for enabling its axial translation.

In use, X-ray applicator 4 may positioned using the articulated arm 4a. In particular, articulated arm 4a may have a rotational joint 6a that coupled to the base 2 (FIG. 1a) of the mobile X-ray unit 10, and a ball joint 6b, coupled to the X-ray applicator 4. The position of the X-ray applicator 4 may be determined using the indicators discussed above, and may be fixed using built-in brakes (not shown) provided in the joints 6a, 6b. After this, the rotating portion 9a may be moved for allowing an axial displacement of the X-ray tube. In this way the X-ray applicator 4 may be gradually brought closer to the target region. In one embodiment, the rotating portion 9a may be adapted to move about 1-4 cm.

Figure 7B:
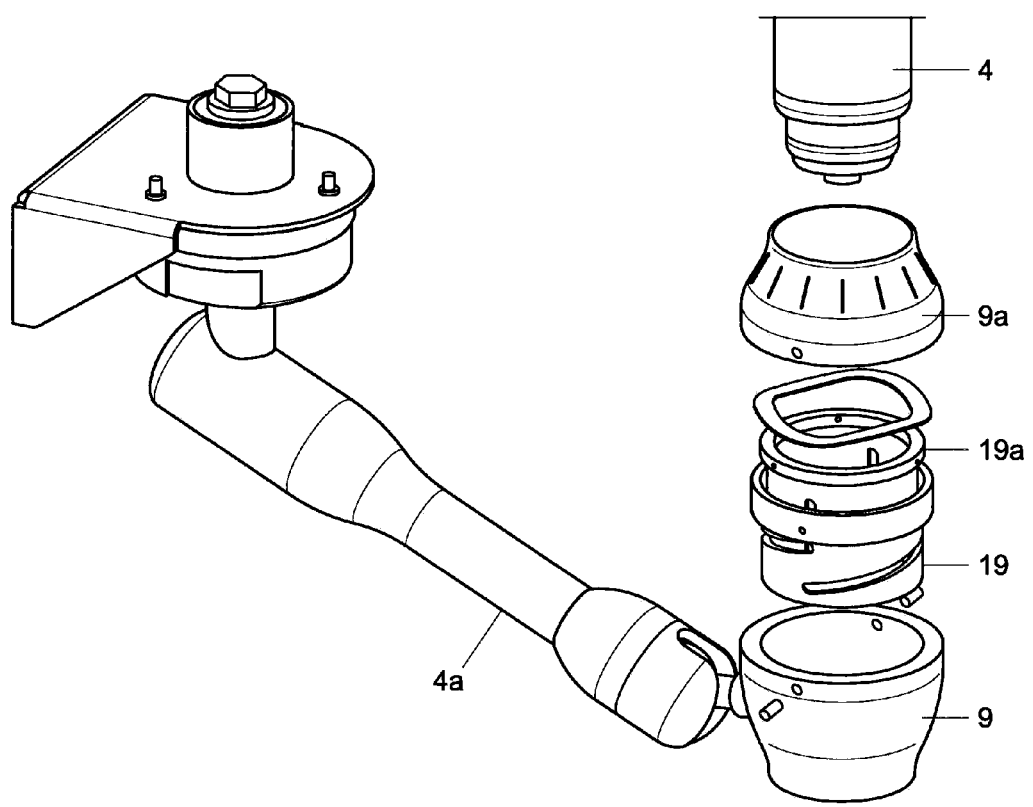
FIG. 7b presents an exploded view of the mechanism configured to finely adjust an axial position of the X-ray applicator of FIG. 7a, according to embodiments of the disclosure.

FIG. 7b presents an exploded view of the mechanism of FIG. 7a. In this figure, it is shown that the X-ray applicator 4 may be disposed within the axial displacement mechanism, which may include a rotating body 9a, an adapter 19a for engaging the X-ray applicator 4, a screw mechanics 19, and a holder 9 connected to the articulated arm 4a. It will be appreciated, however, that other mechanisms for axially translating the X-ray applicator may be contemplated, including, but not limited to, telescopic mechanisms.

Figure 8:
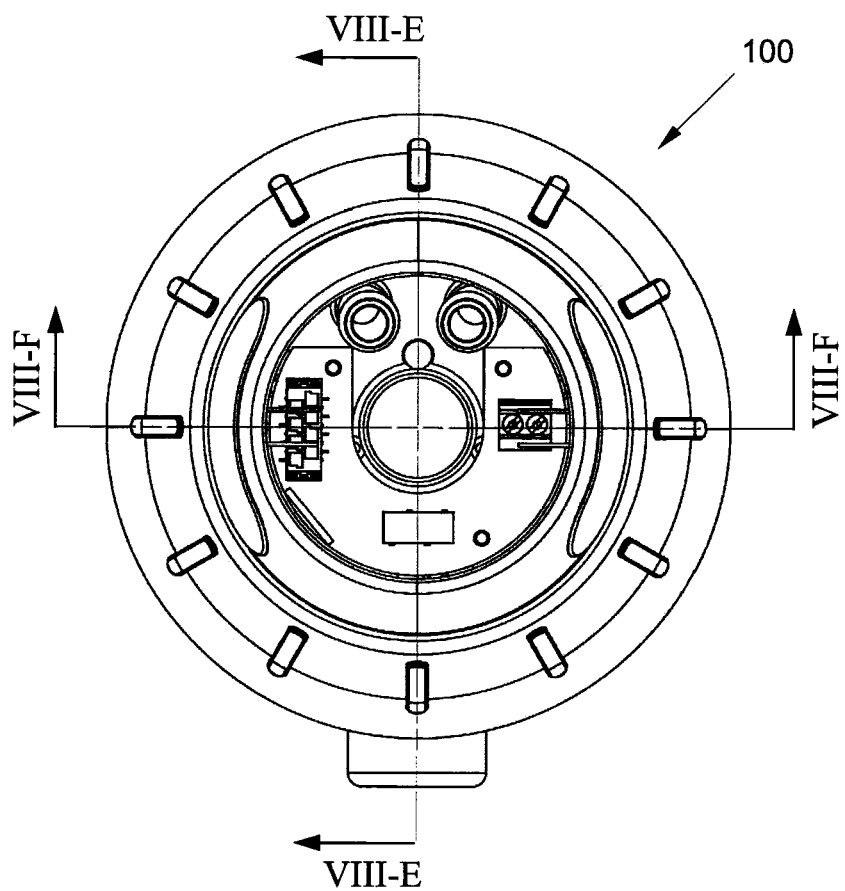
FIG. 8 presents an end view of the X-ray tube, according to embodiments of the present disclosure.

FIGS. 8, 8E-E, and 8F-F, illustrate various views of the X-ray tube. The X-ray tube 100 may have a body 102 enclosing at one end an end window 104 through which the X-rays pass. See FIG. 8, cross-section E-E. The end window 104 may be made from a thin sheet of Beryllium metal. An applicator cap 106 may be positioned over the end window 104 so as to covering the end window 104 and protect end window 104. Applicator cap 106 may be made from a plastic material. The applicator cap may be manufactured from PVDF (polyvinylidene fluoride) and has a thickness of about 0.4-0.7 mm, and preferably 0.6 mm, across the window portion. Alternatively, the applicator cap 106 may be manufactured from PPSU (polyphenylsulfone) and have a thickness of about 0.3-0.6 mm, and preferably 0.5 mm, across the window portion.

In the tube body 102, a target 108 may be located at a range between 4 and 10 cm from the collimator 130, and preferably between 4 and 5 cm from the collimator 130 (see FIG. 7, cross-section F-F). It will be appreciated that this distance is measured between the outer surface of the target 108 and a midplane of the collimator 130. The target 108 may be made from Tungsten metal to provide the desired X-ray spectrum. The tungsten tip of the target 108 may be mounted on a large anode assembly 110 which also serves to dissipate the heat created from the generation of the X-rays in the target 108. Most of the anode assembly 110 is made from copper. The cathode 112 (see FIG. 7, cross-section F-F) may be located slightly off—axis near the end window 104. Electrons emitted from the cathode are accelerated across the gap by the potential difference between the cathode and anode, in this case set at about 70 kV, to the target 108 where the impact causes the generation of X-rays in a known manner. X-rays emitted from the target 108 pass through a beam hardening filter 122 before passing through a collimator 130 and an exit surface 124 on an applicator cap 106. The collimator 130 may be housed in a suitable collimator receptacle 128.

The anode assembly 110 may be mounted in the body 102 and electrically insulated. One of a number of known techniques and materials may be used to provide the desired level of insulation between the anode assembly 110 and the body 102.

As is well known in the art, the production of X-rays generates large amounts of waste heat. Accordingly, it may be necessary to cool the X-ray tube 100 in order to maintain it at a safe temperature. Various cooling mechanisms are known and used in the art. In one embodiment, the X-ray tube 100 may be cooled by cooled water forced around the anode region. Cooled water enters the back of the tube by a first conduit 116 and leaves by a second conduit 118 (see FIG. 7, cross-section F-F). The water cooling circuit is a closed loop circuit, with the water leaving the tube assembly 105 to be cooled by a remote cooler (not shown) before returning to the X-ray tube 100. It is contemplated that oil or another liquid may be used as the cooling medium. It is also known that a pressurized gas may be used as an effective coolant in some applications.

As is known in the art, X-rays are generated and emitted in all directions, however the body 102 of the X-ray tube 100 and other internal components will tend to reduce the amount of radiation emitted from the body 102 of the X-ray tube 100 to a minimum, with most of the radiation emitted from the end window 104. The thickness of the shielding provided by the body 102 may be designed so that it provides at least the minimum level of shielding required for safe use by the operator.

A high voltage cable assembly 120 may be connected to the anode assembly 110. The high voltage cable assembly 120 may be connected to flexible cable means (not shown) which in turn may be connected to a high voltage power supply.

A radiation detector 114 may be placed outside the path of the X-ray beam emitted from the target 108 and passing through the end window 104. This detector can be any known form of radiation detector. In one embodiment, the radiation detector may be a hardened semi-conductor connected to an amplifier. The radiation detector 114 may detect when the tube 102 is working and emitting X-ray energy. Output from the detector 114 may connected to a control unit, and the output signals from the detector 114 may be used to provide an optical indication to a user of whether the tube is operating or not. By this means an X-ray detector 114 may be provided which may be used to detect if the X-ray tube is on or off.

With further calibration of the radiation detector 114, it may be possible to determine and calculate the X-ray dose administered to the patient during the treatment. By this means it may be possible to have a real time dosimetry measurement system, in which the precise amount of radiation dose administered can be determined. Once the dose rate is known, a treatment plan can be modified during treatment. This may be advantageous because it may enable a very accurate and carefully controlled dose of X-rays to be administered.

In order to enable the X-ray tube 100 to be placed accurately over a tumour, a tumour illumination device may be is used. The tumour illumination device may include a plurality of lights 126 placed around the circumference of the X-ray tube 100 near the end window 104. When in use, the lights shine onto the skin of the patient. Since the lights 126 are positioned around the circumference of the tube body 102, at a short distance from the end of the X-ray tube 100, they create a circle of light with a sharp cut off of the inner part of the circle. In this way, the position of the lights on the tube body 102 may create a shadow. This shadow circle may be used to indicate the region which will be subject to irradiation when the X-ray tube 100 is turned on. It should be appreciated the area within the circle may not be completely dark; the ambient light may be able to enter the shadow region.

In some embodiments, the lights 126 are white LEDs which can be bright enough to clearly illuminate the target region but do not generate large amounts of heat and have very long lives. The lack of heat generation is important because the lights will be in close proximity to the skin of the patient, and so it is important to minimise the risk of burning or other damage to the skin. Other colours of LEDs may be used. Alternatively, other light sources could be used, such as known filament lamps or even a remote light source connected to the ring by fibre optic cables.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A mobile X-ray unit comprising:
   a base having a control unit configured to control an X-ray applicator and a power supply configured to supply power to the X-ray applicator;
   an articulated arm associated with the base and coupled to the X-ray applicator, the X-ray applicator having an X-ray tube including a target for generating an X-ray beam, a collimator for shaping the X-ray beam, and an exit surface through which the shaped X-ray beam is configured to exit the X-ray tube; and
   at least one light source configured to illuminate at least a portion of the X-ray beam emitted from the exit surface.

2. The mobile X-ray unit according to claim 1, wherein the at least one light source is an array of light sources arranged concentrically around the X-ray applicator.

3. The mobile X-ray unit according to claim 2, wherein the X-ray beam has a longitudinal axis, and wherein each light source is arranged to emit a beam of light towards the longitudinal axis at a pre-determined distance from the exit surface of the X-ray tube.

4. The mobile X-ray unit according to claim 1, wherein the light source is disposed inside the X-ray applicator, and wherein the light source is configured to emit a light beam that is intercepted by the collimator so as to generate an image of an X-ray field emitted from the exit surface of the X-ray tube.

5. The mobile X-ray unit according to claim 1, further including at least one optical fiber configured to deliver light from the light source for interception by the collimator.

6. The mobile X-ray unit according to claim 5, wherein the at least one light source is connected to a plurality of optical fibers disposed above the collimator in the X-ray applicator, the optical fibers being configured to illuminate an opening of the collimator.

7. The mobile X-ray unit according to claim 1, wherein the at least one light source is configured to emit a light beam so as to delineate a longitudinal axis of the X-ray beam.

8. The mobile X-ray unit according to claim 1, wherein the at least one light source is a laser.

9. The mobile X-ray unit according to claim 1, wherein the at least one light source is a light emitting diode (LED).

10. The mobile X-ray unit according to claim 1, wherein the at least one light source is configured to provide a contrast image of at least a portion of the X-ray beam.

11. The mobile X-ray unit according to claim 1, wherein the collimator is provided with identification devices configured to generate a signal representative of characteristics of the collimator and transmit the signal to the control unit.

12. The mobile X-ray unit according to claim 1, wherein the collimator is configured to be received in a receptacle having a resistive path, the collimator having a set of projections configured to cooperate with the resistive path of the receptacle for generation the signal.

13. The mobile X-ray unit according to claim 1, further including a set of collimators each having unique identification devices.

14. The mobile X-ray unit according to claim 1, further including a radiation detector for detecting the X-ray beam.

15. The mobile X-ray unit according to claim 14, wherein the radiation detector is configured to generate a control signal upon generation of the X-ray beam.

16. The mobile X-ray unit according to claim 1, further comprising a temperature sensor configured to measure a temperature of a surface of one of the X-ray tube and the X-ray applicator.

17. The mobile X-ray unit according to claim 1, further including an applicator cap for covering at least an exit surface of the X-ray applicator.

18. The mobile X-ray unit according to claim 17, wherein the applicator cap is disposable after a single use of the X-ray applicator.

19. The mobile X-ray unit according to claim 17, wherein a thickness of the applicator cap in a direction of the beam propagation is sufficient for substantially eliminating electron contamination from the X-ray beam.

20. The mobile X-ray unit according to claim 1, wherein the power supply is operable in the range of 60-75 kV for generating the X-ray beam.

21. The mobile X-ray unit according to claim 20, wherein the power supply is operable for delivering power of about 200 W in use.

22. The mobile X-ray unit according to claim 1, wherein the X-ray applicator is connected to the base by a flexible cable, and wherein the flexible cable is disposed in a displaceable panel.

23. The mobile X-ray unit according to claim 22, wherein the at least one light source is disposed in the displaceable panel.

24. The mobile X-ray unit according to claim 20, wherein the at least one light source is disposed in the base.

25. The mobile X-ray unit according to claim 22, wherein the displaceable panel includes a user interface for controlling the X-ray unit.

26. The mobile x-ray unit according to claim 1, wherein the at least one light source is configured to illuminate a two-dimensional portion of the surface irradiated by the X-ray beam.

27. A method for visually delineating an X-ray beam emitted from a mobile X-ray unit, the mobile X-ray unit including a base having a control unit configured to control an X-ray applicator and a power supply configured to supply power to the X-ray applicator, the mobile X-ray unit further including an articulated arm associated with the base and coupled to an X-ray applicator, the X-ray applicator having an X-ray tube including a target, a collimator, and an exit surface, the method comprising:
generating an X-ray beam;
shaping the X-ray beam; and
illuminating at least a portion of the surface irradiated by the shaped X-ray beam emitted from the exit surface.

28. The method according to claim 27, further including a light source.

29. The method of claim 28, wherein the light source is disposed in the X-ray applicator.

30. The method according to claim 28, wherein the light source is disposed on the X-ray applicator.

31. The method according to claim 28, wherein the light source is configured to generate a light field providing indication of a two-dimensional area of the X-ray beam.

32. The method according to claim 28, wherein the light source is configured to delineate a longitudinal axis of the X-ray beam.

* * * * *